United States Patent
Rea

(10) Patent No.: US 10,517,493 B2
(45) Date of Patent: Dec. 31, 2019

(54) DETECTION OF REVERSIBLE NERVE INJURY

(71) Applicant: NEUROVISION MEDICAL PRODUCTS, INC., Ventura, CA (US)

(72) Inventor: James Lee Rea, Ventura, CA (US)

(73) Assignee: Neurovision Medical Products, Inc., Ventura, CA (US)

( * ) Notice: Subject to any disclaimer, the term of this patent is extended or adjusted under 35 U.S.C. 154(b) by 0 days.

(21) Appl. No.: 15/407,529

(22) Filed: Jan. 17, 2017

(65) Prior Publication Data

US 2017/0119268 A1    May 4, 2017

Related U.S. Application Data

(62) Division of application No. 14/098,419, filed on Dec. 5, 2013, now Pat. No. 9,545,208.

(60) Provisional application No. 61/734,730, filed on Dec. 7, 2012, provisional application No. 61/905,068, filed on Nov. 15, 2013.

(51) Int. Cl.
    *A61B 5/04*     (2006.01)
    *A61B 5/0488*   (2006.01)
    *A61B 5/00*     (2006.01)

(52) U.S. Cl.
    CPC ........ *A61B 5/04001* (2013.01); *A61B 5/0488* (2013.01); *A61B 5/4029* (2013.01); *A61B 5/7282* (2013.01); *A61B 5/742* (2013.01); *A61B 5/746* (2013.01)

(58) Field of Classification Search
    CPC .............. A61N 1/0556; A61N 1/36135; A61N 1/36053; A61B 5/04001; A61B 5/0488; A61B 5/4029; A61B 5/4041; A61B 5/7282; A61B 5/742; A61B 5/746
    USPC ................................................. 600/546, 547
    See application file for complete search history.

(56) References Cited

U.S. PATENT DOCUMENTS

| | | |
|---|---|---|
| 2006/0217631 A1 | 9/2006 | Kong |
| 2008/0300655 A1 | 12/2008 | Cholette |
| 2009/0209896 A1 | 8/2009 | Selevan |
| 2010/0145222 A1* | 6/2010 | Brunnett ............ A61B 5/04001 600/554 |
| 2011/0130429 A1 | 6/2011 | Borgens |
| 2012/0130269 A1 | 5/2012 | Rea |

OTHER PUBLICATIONS

Supplemental European Search Report in European Patent Application No. 13861016.7 dated Jun. 22, 2016.

\* cited by examiner

*Primary Examiner* — Devin B Henson
(74) *Attorney, Agent, or Firm* — M.J. Ram and Associates; Michael J. Ram

(57) ABSTRACT

A system for monitoring relative nerve health and the presence of neuropraxia is described. The system utilizes the integration of a waveform function of an elicited or monitored nerve response to provide an indication of the strength of a detected signal from a nerve and thus the relative health and integrity of the nerve. In some embodiments motor nerve stimulation innervates muscle and an EMG waveform is obtained in response thereto. The integration under the waveform is expressed and an indexed value indicating a percentage of a certain threshold value. Methods set forth provide a more reliable status of a nerve in real-time and allow action to be taken to reduce neuropraxia or prevent permanent nerve damage.

17 Claims, 4 Drawing Sheets

DETECTION OF REVERSIBLE NERVE INJURY

CROSS REFERENCE TO RELATED APPLICATIONS

The present application is a Divisional of U.S. patent application Ser. No. 14/098,419, filed on Dec. 5, 2013, now U.S. Pat. No. 9,545,208, issued Jan. 17, 2017, which also claims the benefit of U.S. Provisional Application Ser. No. 61/734,730 to James Lee Rea, entitled METHOD OF DETECTING REVERSABLE NERVE INJURY, filed on Dec. 7, 2012 and U.S. Provisional Application Ser. No. 61/905,068 to James Lee Rea, also entitled METHOD OF DETECTING REVERSABLE NERVE INJURY, filed on Nov. 15, 2013. Both of these provisional applications are hereby incorporated herein in its entirety by reference, including the drawings, charts, schematics, diagrams and related written description.

BACKGROUND

Field of the Invention

The present invention relates generally to methods for the monitoring of nerves and specifically to the detection of reversible nerve injury.

Description of the Related Art

Reversible Nerve Injury, known as "neuropraxia," is a medical condition where a motor nerve is stressed, often occurring during surgery, by surgical trauma, stretching, and/or devascularization. Because neuropraxia is preventable, it is of value to identify degrees of neuropraxia early and to quantify the extent of nerve injury. An insult capable of causing neuropraxia may be capable of resulting in irreversible nerve palsy. This is an additional concern and reason for detecting and preventing neuropraxia.

Historically, neuropraxia prevention was attempted by Intraoperative Nerve Monitoring (IONM). This technique involved collection of electromyographic responses (EMG) from the target muscle innervated by target nerves and "monitoring" those responses for waveform patterns typical of irritation of the nerve. IONM response might include sustained EMG activity due to stretch or tension on the nerve from retraction. IONM EMG response of significance might also include bursts of activity associated with a dissection recognized as being risky by the surgeon (surgeon identified response) or activity which is seen by an individual monitoring the IONM equipment, such as visual or auditory feedback from the EMG.

A relatively new modality of neuropraxia detection is the observation of evoked responses of the nerve. In this method, a nerve response is "evoked" by an electronic nerve stimulator and the response is examined for indications of the functional integrity of the stimulated nerve. Indications might include latency of response (the time from the stimulation to the onset of the evoked response), the morphology of the response waveform, and the amplitude of the evoked response voltage. This type of testing can be automatic by "ping" testing with an implantable stimulator probe, or manually by the surgeon using a hand held stimulation probe. FIG. 1 depicts an example of a waveform 100 of an evoked EMG response 102 wherein the response plotted on a graph wherein the y-axis 104 represents electric response output and the x-axis 106 represents time. Prior art methods observe changes in the amplitude (peak-to-peak) values 108 or differentiation (i.e. the slope of the waveform) to infer the onset of neuropraxia. However, this is not a completely accurate representation of the strength of a nerve response or the integrity of the monitored nerve.

Present methods of Neuropraxia detection, especially those requiring implantation of dedicated stimulation devices and those relating to voltage response algorithms may be costly, time consuming, suffer from lack of reliability, and counter-intuitive in conceptualization, possibly leading to misdiagnosis during the stress of performing live surgery. In addition, voltage responses do not always truly reflect the degree of injury to a nerve, the response also being dependent on the strength of stimulation, the size and excitability of the target muscle, and the effectiveness of the pickup electrodes. Of particular disadvantage is the fact that nerve response can occur without actual muscle movement, giving a false negative indication of advancing neuropraxia. A more reliable and efficient method for monitoring the heath and response strength of a nerve is therefore needed.

SUMMARY

Described herein are novel methods for detecting and quantifying neuropraxia. In contrast to the prior art methods described above, methods incorporating features of the present invention utilize the mathematical integration under a waveform curve resulting from a monitored or elicited nerve response. Integration is much more reliable and accurate indication of the strength of a nerve response, and thus the underlying health of the nerve, than are the prior art methods of merely monitoring waveform amplitude or slope.

The numerical values obtained by integration can then be compared to a threshold value, providing useful information to a surgeon or physician regarding the relative health of the monitored nerve. In some embodiments, an index value can be established by comparing the value of the integrated response to the threshold response. This index value, for example, can be displayed as a percentage of the predetermined threshold.

In a first embodiment incorporating features of the present invention a method of detecting neuropraxia in a nerve comprises the use of integration of a waveform.

In other embodiments incorporating features of the present invention, a method of detecting the health of a nerve through measuring a nerve response comprises the steps of stimulating a nerve and eliciting a response, detecting the response and presenting the response as the intensity of the waveform over time, and integrating the waveform and obtaining an integration value.

In still other embodiments incorporating features of the present invention, a method of detecting neuropraxia in a motor nerve comprises the steps of stimulating a motor nerve and eliciting a response, detecting the response from a muscle innervated by the motor nerve, presenting the response as the intensity of a waveform over time, integrating the area under the waveform and obtaining an integration value, and comparing the integration value to a predetermined threshold value.

These and other further features and advantages of the invention would be apparent to those skilled in the art from the following detailed description, taking together with the accompanying drawings, in which:

DETAILED DESCRIPTION

Figure 1:
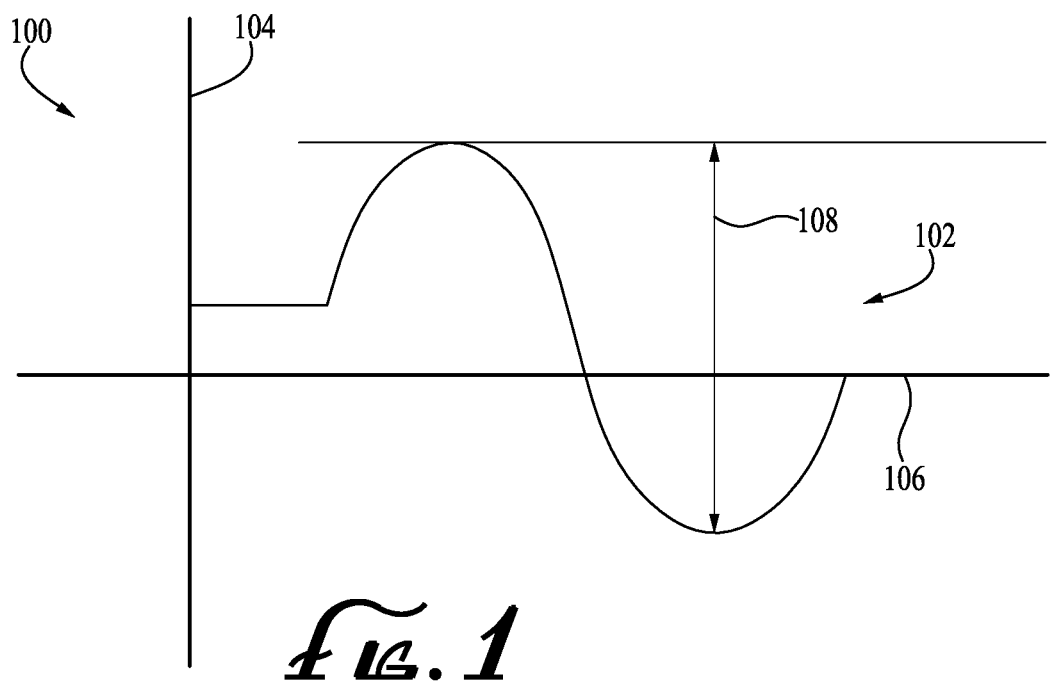
FIG. 1 is graphical representation of a prior art method of using a waveform detecting a nerve response utilizing peak-to-peak voltage amplitude of a waveform.

Methods incorporating features of the present invention may involve evoked nerve stimulation and/or monitoring free-run (non-stimulated) responses. The resulting nerve responses can be monitored either at the site of the nerve directly and/or via the monitoring of an EMG response of a muscle innervated by the nerve to be monitored. Evoked stimulation methods, using manual stimulation probes and/or implanted stimulator probes, utilize an algorithm based upon mathematical integration of the resultant response waveform.

In some embodiments, such probes or electrodes can be incorporated into or utilized in conjunction with a surgical tool, for example a surgical dissector, and can indicate through change in monitored nerve response output, the proximity of the surgical instrument to the underlying nerve and the effect of the instruments or surgical procedure on nerve health. Furthermore, a nerve can be monitored so that the general health and function of the nerve provides an indication of the overall level of trauma the nerve is undergoing during a medical procedure such as a surgery. This provides surgeons with useful advanced warnings of potentially impending neuropraxia which the surgeon can then take necessary steps to prevent or minimize.

Integration, or measurement of the area under the waveform, is more closely correlated with the power of nerve/muscle response than is the peak voltage or peak to peak voltage amplitude of the response utilized in the prior art. The power, or electrical mass action of the response reflects the number of functioning neurons in the stimulated nerve and the number of activated muscle fibers in the target muscle.

After detection, recording, and quantification of the above mentioned integrated response, the information can be displayed for use by users, such as medical practioners, in a useful and intuitive manner. One such procedure, is a "percentage integration" where the actual integrated value is displayed as a percentage of the integration threshold for a typical or reference single stimulation response.

The above integration threshold value can be determined in a number of ways, for example, using empirical data regarding the nerve in question with a particular waveform integration value corresponding to the onset of neuropraxia. For example, a certain voltage output integrated over time from an EMG reading that is typically representative of the onset of nerve damage for a particular nerve, such as the recurrent laryngeal nerve, can be set as the threshold value of this nerve. Thresholds can be determined empirically or by repeated collection of clinical data or by logical selection of a threshold based on the expected clinical usefulness of various threshold values.

The voltage output reading can be converted to a percentage with an index value of 100%, a number less than 100% representing the onset of neuropraxia which can be used to trigger an alert such as a beep or other alarm in a monitoring device. A baseline integration value of the initial reading of the nerve can be used to provide a unique threshold. An integrated value of several times the threshold value, for example, an index of 450%, would indicate a healthy nerve. As a medical procedure and corresponding nerve monitoring progresses, the index value may be reduced below 100%, indicating trauma, strain or damage to the monitored nerve. An index value declining to 100% or lower (the threshold value) can then be investigated as indicating possible Neuropraxia or onset of permanent nerve damage.

During monitoring of a nerve under conditions in which neuropraxia is a significant possibility, for example, during surgery, a susceptible nerve can be repeatedly stimulated, the percentage integration indicate impending neuropraxia by a reduction in the index number, thus providing an early warning to the user when the procedure being performed is in danger of injuring the nerve.

A free-run (non-stimulated) method of detecting neuropraxia can also involve the same integration of the waveform. In this method, free-run EMG is sampled for various periods of time, either on schedule or randomly in response to recognized non-repetitive events, and the waveform integration is determined. Based on the particular algorithm employed, which may be adapted to a specific medical problem or location in the body, an index or threshold of the integrated value is identified and displayed and/or an alert signal is generated to provide clinically useful data and/or as a warning.

An example algorithm incorporating features of the present invention can comprise a series of steps wherein a stimulation, such an an electrical stimulation pulse, is generated by a stimulating component. A stimulating electrode or probe, for example, a stimlating electrode or probe on a surgical instrument can be used, the stimulation is applied to a motor nerve, a response is elicited and a sensing electrode detects the response from the muscle. An EMG Machine then produces a waveform reading of the response, the EMG waveform function is integrated over time, producing a realtime integration value. The realtime integration value can be divided by the threshold value for for the stimulated nerve and the value is displayed for use by a viewer.

It is understood that while the present disclosure discuss the detection of neuropraxia, methods incorporating features of the present invention can be utilized to not only detect impending nerve damage, but also detect the relative health and signal strength of an underlying nerve. In addition, a permanent digital or printed time-based record of the nerve response during the procedure can be generated.

It is also understood that while this present disclosure uses the terms "surgeon," "surgeons," "physician," and/or "physicians," that these terms can include any user of methods incorporating features of the present invention including, but not limited to nurses, IOM technicians and anesthesiologists. The fact that methods according to the present disclosure are particularly applicable to medical and surgical applications does not limit the embodiments herein and any such methods can be performed by any user attempting to monitor the heath and integrity of a nerve and/or to detect and/or prevent neuropraxia.

Throughout this disclosure, the preferred embodiments herein and examples illustrated are provided as exemplars, rather than as limitations on the scope of the present disclosure. As used herein, the terms "invention," "method,"

"present method" or "present invention" refers to any one of the embodiments incorporating features of the invention described herein, and any equivalents. Furthermore, reference to various feature(s) of the "invention," "method," "present method" or "present invention" throughout this document does not mean that all claimed embodiments or methods must include the referenced feature(s).

It is also understood that when an element or feature is referred to as being "on" or "adjacent" another element or feature, it can be directly on or adjacent the other element or feature or intervening elements or features that may also be present. Furthermore, relative terms such as "outer", "above", "lower", "below", and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present invention. As used herein, the term "and/or" includes any and all combinations of one or more of the associated list items.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments of the invention. As such, variations from the illustrated signal flow, for example, are contemplated. Embodiments of the invention should not be construed as limited to the particular illustrated embodiments herein but are to include deviations may be necessary to adopt to a different engine design.

Figure 2:
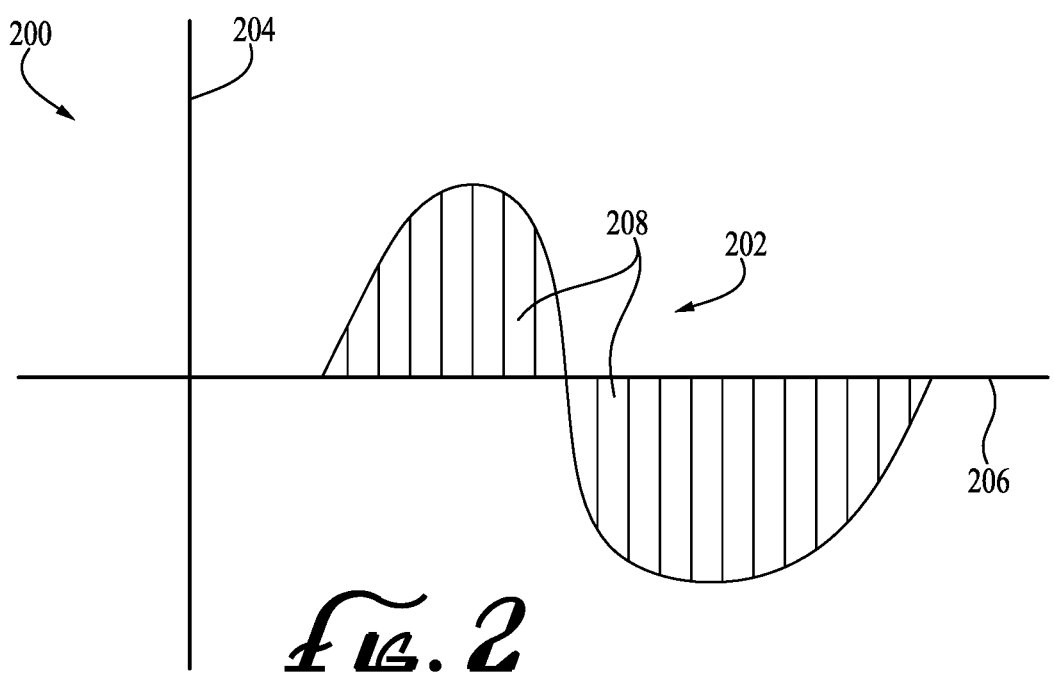
FIG. 2 is graphical representation of a method of detecting a nerve response utilizing integration of a waveform function from an evoked nerve response incorporating features of the present invention.

FIG. 2 depicts an example of a waveform reading 200 of an evoked EMG response 202 wherein the response is plotted on a graph with the y-axis 204 representing electric response output and the x-axis 206 representing time. The response in FIG. 2 is elicited by stimulating a motor nerve innervating a particular muscle and monitoring the EMG output at the given muscle. Unlike the prior art example in FIG. 1, methods incorporating features of the present invention utilize integration of the area under the waveform 208 in calculations to determine the strength of a response from a nerve.

Figure 3:
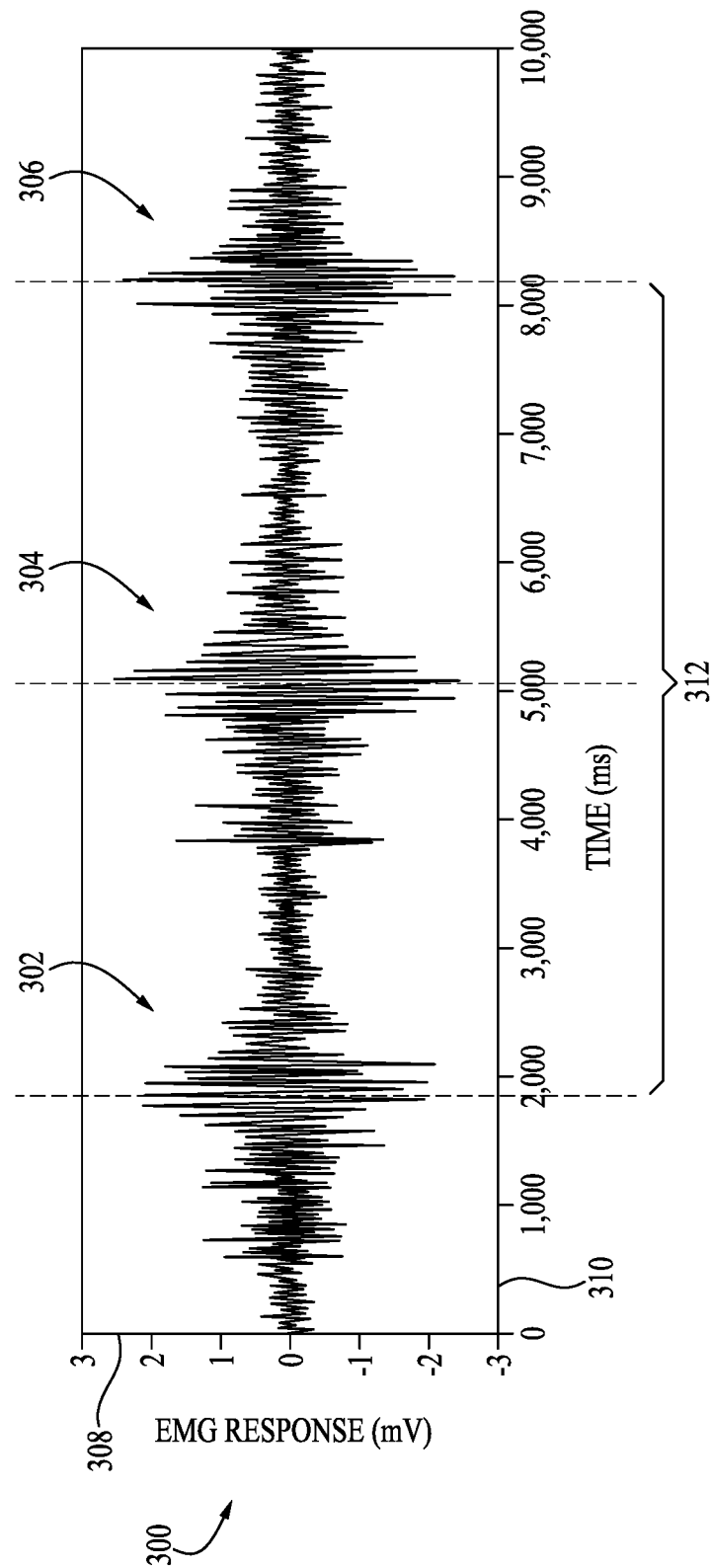
FIG. 3 is graphical representation of a method of detecting a nerve response utilizing integration of an actual waveform generated from a free-run nerve response incorporating features of the present invention.

In addition to utilizing evoked responses, integration of a response can also be utilized with a free-run EMG response reading. FIG. 3 depicts an example waveform 300 reading of a plurality of free-run EMG responses 302, 304 and 306. The responses 302, 304, 306 are plotted on a graph wherein the y-axis 308 represents electric response output in voltage and the x-axis 310 represents time in miliseconds. In utilizing the free-run waveform 300, EMG is sampled for various periods of time, either on a scheduled basis as shown by sampling points 312, or randomly in response to recognized non-repetitive events, for example, various stages in a surgical procedure being performed. Integration of the function of this free-run EMG responses 302, 304 and 306 are performed similarly to the evoked EMG response 202 in FIG. 2 above and shown for individual sampling points 312 or an average of several sampling points.

A power index of threshold values for the nerve or muscle being monitored can be established for comparison with the information gained from the above mentioned integrated waveforms. If all other factors are the same (i.e. level of stimulation, level of anesthesia, etc.), the repeated stimulation of a monitored nerve, especially at the same anatomical spot, can indicate, by reduction in the level of the response as represented by a change in the integration value in FIG. 2 above, that neuropraxia is occurring and the extent of neuropraxia. The integrated response value is used to determine the presence of a compound motor action potential response by an empirically derived compound action potential (CAP) threshold. Monitored responses differing from the threshold value alert the user, for example, causing an alert such as an audio, visual or various other observable warning signals, such as light of varying colors, indicating that a stimulating dissector is in proximity to a nerve. Such a stimulating dissector can include a surgical instrument modified to supply the stimulation component of methods incorporating features of the present invention.

By using stimulating dissectors, some methods incorporating features of the present invention add proactivity for nerve proximity to a surgical dissection. By displaying the CAP integral as a percentage of the CAP threshold, methods according to the present disclosure create a power index for nerve/muscle response as a percentage of the level of response that minimally causes the alert for localization. Repeated stimulation of the nerve under the same conditions and the generation of the response in comparison to the threshold provides the surgeon with a real-time index of Neuropraxia.

The power index, being quantitative, is much more valuable to a surgeon than a simple loss of stimulated responses, can be made immediately available to the surgeon for troubleshooting, and can be stored in an archival playback file. Nerve monitoring data can be displayed for example using a PC display or by a "dashboard" clip-on tablet computer on an IV pole at the surgeon's eye level. For example, in practice, a healthy recurrent laryngeal nerve (RLN) when first stimulated delivers approximately 450% of the threshold value. In the presence of nerve fatigue the number drops throughout the procedure. A response approaching 100% (i.e. the threshold value) is an indication of possible impending nerve injury.

Figure 4:
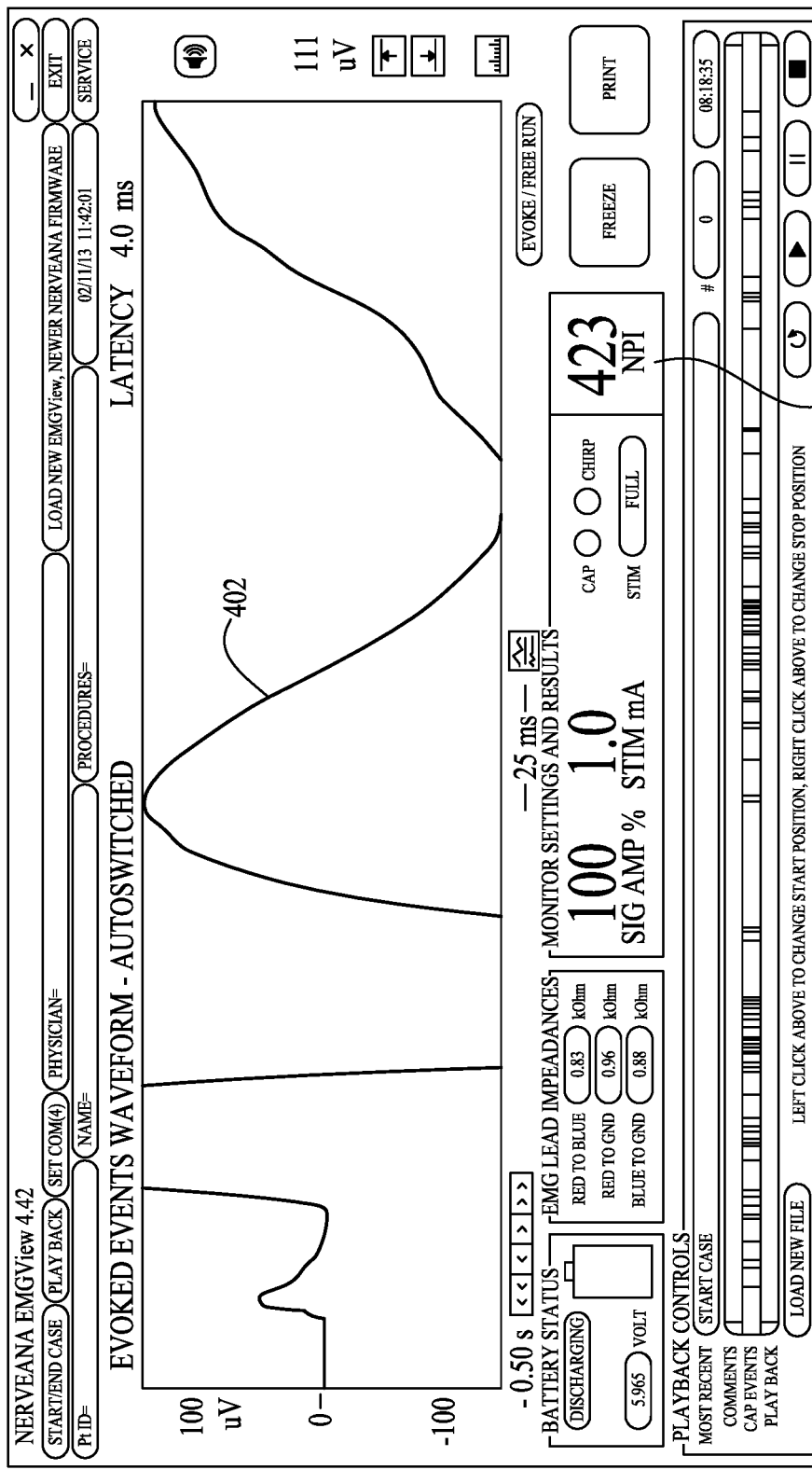
FIG. 4 is an example display generated using a neuropraxia detection and evaluation systems incorporating features of the present invention.

An example display 400 of the information is shown in FIG. 4. The display 400 depicts a waveform 402 corresponding to an evoked EMG response. A processor, such as a computer, calculates the integral of the function of the waveform, thus determining the area under the waveform. As mentioned above, the integration of the waveform represent a more accurate representation of the health of a nerve, as represented by the nerve electrical signal output, which better corresponds to the number of functioning neurons in the stimulated nerve and the number of activated muscle fibers in the target muscle.

Another feature of display 400 is the presentation of the index value 404 displayed as a percentage of a predetermined threshold. The display indicating an index value of 423 (423%), represents a healthy nerve with an output significantly higher than a threshold value of 100 (100%).

Figure 5:
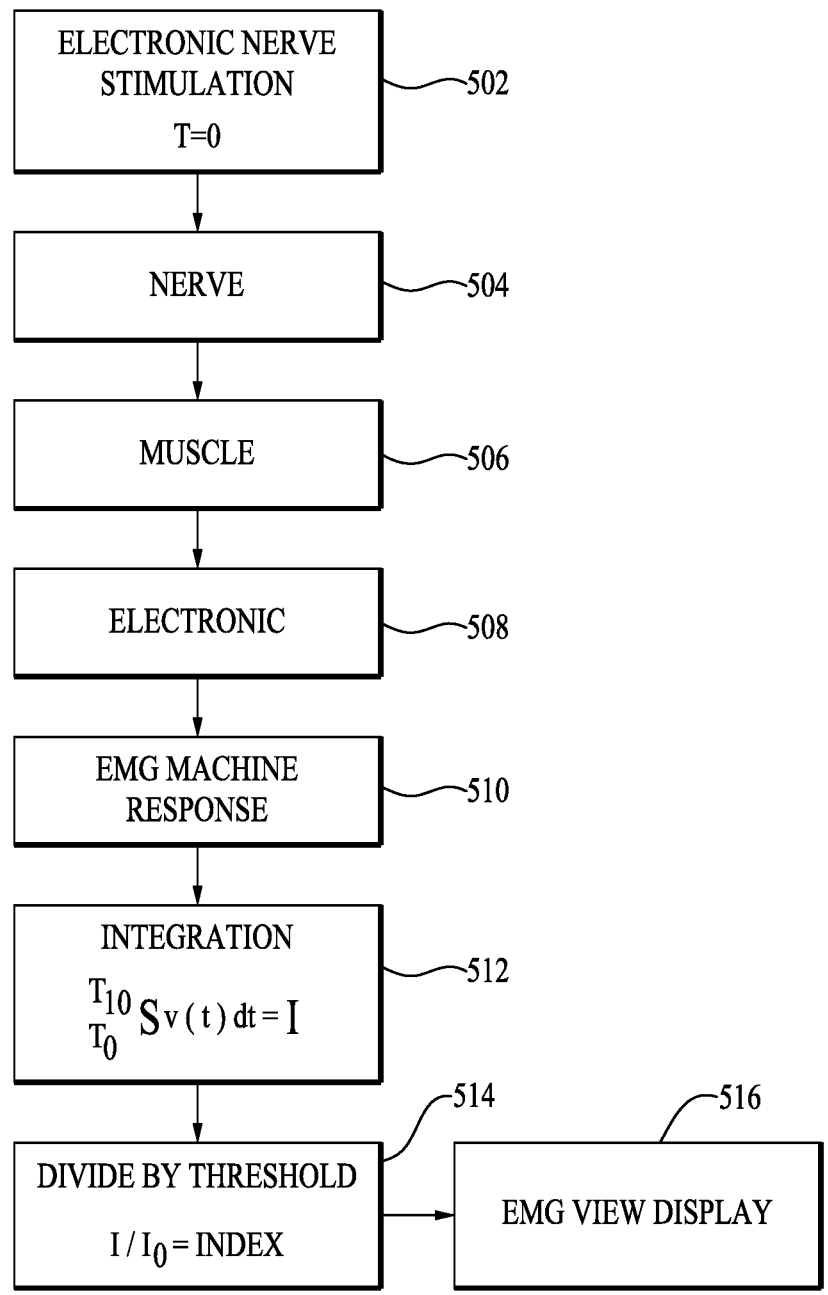
FIG. 5 is a flow chart depicting the steps in an embodiment of one method of detecting neuropraxia incorporating features of the present invention.

An example of nerve monitoring incorporating features of the present invention includes the logic path shown in FIG. 5. A first step 502 involves a stimulation, such an electrical stimulation pulse, being generated by a stimulating component, such as a stimulating electrode or probe. The stimulating component can be affixed or used in conjunction with a surgical instrument, for example, a surgical dissector or an endotracheal tube.

In a second step 504, the stimulation is applied to a muscle or nerve with the preferred and more accurate action being to apply the stimulation to a nerve. In a third step 506, a muscle response is elicited, either through direct stimulation or through the stimulation of an innervating nerve as performed in the second step 504 above.

In a fourth step 508, a sensing component, for example a sensing electrode, detects the response from the muscle that was stimulated in the third step 506. In a fifth step 510 an EMG Machine produces a waveform reading of the muscle response. In a sixth step 512, the EMG waveform function is integrated over time, producing a real-time integration value (I). In some embodiments, this real-time integration value is recalculated every 4 seconds and can be displayed serially or averaged over a selected time period.

In a seventh step 514, the real-time integration value (I) is divided by the threshold value for generation of a compound action potential ($I_0$) for the stimulated nerve; this calculation produces an index value (for example a Nerveana® Power Index "NPI") which is a percentage of the threshold value as is discussed above. In an eighth step 516, the index is displayed for observation by the user.

As a further example, a single use is described. A system incorporating features of the present invention was utilized with a 10 year old, 36 Kg, Caucasian female who was diagnosed with a locally metastatic papillary thyroid carcinoma presented for total thyroidectomy and central neck dissection. Her past medical history was significant for ADHD, asthma, and short stature. She previously had tympanostomy and adenotonsillectomy. Her medications included methylphenidate, cetirizine, nasonex nasal spray, levalbuterol inhaler and albuterol. Except for a short stature and a palpable left thyroid nodule, her physical examination was normal. A neck ultrasound showed a heterogeneous nodule measuring 1.9×1.5×1.2 cm in the left thyroid lobe. The right thyroid lobe was normal. A prior fine needle aspiration was diagnostic for papillary thyroid carcinoma.

Following premedication with midazolam 12 mg, anesthesia was induced with sevoflurane inhalation and a peripheral IV catheter was placed. Anesthesia was deepened with propofol and fentanyl and a direct laryngoscopy was performed. The trachea was intubated with a 6.0 mm cuffed endotracheal tube with a LSE 500 ms Dragonfly® single channel electrode (Neurovision Medical Products, Ventura, Calif., USA). Correct electrode position for monitoring the recurrent laryngeal nerve was confirmed using a Glidescope™ video laryngoscope. The electrode was then connected to the Nerveana® monitoring unit (Neurovision Medical Products). The output from the monitoring unit was visualized on a laptop computer with EMG Viewer software as described herein programmed to integrate the area under the response curve and provide an index number reflective of nerve function (NPI).

Anesthesia was maintained with infusions of propofol and dexmedetomidine and incremental doses of fentanyl and morphine. In addition to the standard monitoring for nerve function, the NPI was utilized to further assess recurrent laryngeal nerve (RLN) function over time. The NPI values at baseline and at thirty minutes after baseline for the right vocal cord (RVC) and left vocal cord (LVC) are shown in Table 1. Upon completion of surgery, both RLNs were stimulated proximally and distally relative to the glottis; the NPI values are shown in Table 2. The patient was extubated deep and a post extubation videolaryngoscopy demonstrated normal movement of both vocal cords.

TABLE 1

Initial NPI values

|  | R VC | L VC |
| --- | --- | --- |
| Baseline | 366 | 458 |
| Baseline + 30 mins | 327 | 421 |

TABLE 2

Final NPI values

|  | Right RLN | Left RLN |
| --- | --- | --- |
| Proximal | 389 | 431 |
| Distal | 378 | 333 |

Although the present invention has been described in detail with reference to certain preferred configurations thereof, other versions are possible. Embodiments of the present invention can comprise any combination of compatible features shown in the various figures, and these embodiments should not be limited to those expressly illustrated and discussed. Therefore, the spirit and scope of the invention should not be limited to the versions described above.

The foregoing is intended to cover all modifications and alternative constructions falling within the spirit and scope of the invention as expressed in the appended claims, wherein no portion of the disclosure is intended, expressly or implicitly, to be dedicated to the public domain if not set forth in the claims.

Methods and devices incorporating features of the present invention can also be used for a variety of purposes including surgical and diagnostic purposes. Diagnostic (non-surgical) use of such methods and devices can be made by comparing paired nerves, such as the right side of the body with the left side of the body and by use of trans-cutaneous stimulation or by invasive needle stimulation of the nerve by placing the stimulating needle or probe in proximity of the paired nerves such as to cause a detectable EMG response.

I claim:

1. A monitoring system configured for detecting in a continuously or intermittently stimulated target nerve, in real time, reductions in nerve function resulting from nerve damage, and indicating whether said nerve damage is fully reversible nerve damage, said system configured to monitor an electrical response of the stimulated nerve, said response being a wave form function, and determine an integration value representing an integration of the area under the wave form function generated by said stimulation, wherein
    a. the monitoring system having stored therein a predetermined neuropraxia threshold value representative of nerve responses at or above which a loss of nerve function is fully reversible,
    b. said monitoring system configured to compare said integration value to said predetermined neuropraxia threshold value while the damaged nerve can still be restored to its undamaged state and generate a signal indicating the proximity of the integration value to the predetermined neuropraxia threshold value, signaling a need to discontinue treatment the monitoring system configured for application to an individual at the time of potential nerve damage.

2. The monitoring system of claim 1 in which the wave form function is obtained from a stimulated nerve response or an evoked nerve response.

3. The monitoring system of claim 1, providing said integration value of a free-run EMG or random event wave form nerve response.

4. The monitoring system of claim 1, in which the integration value is compared to the predetermined neuropraxia threshold value and provides a visual or audible signal increasing in intensity as said integration value approaches said neuropraxia threshold value.

5. The monitoring system of claim 1, wherein a nerve response value above the predetermined neuropraxia threshold value is representative of fully recoverable nerve function.

6. The monitoring system of claim 1, wherein a nerve response value below the predetermined neuropraxia threshold value indicates a permanent injury to the nerve.

7. The monitoring system of claim 1, wherein the integration value is calculated and displayed on an intraoperative nerve monitoring (IONM) device.

8. The monitoring system of claim 1, in which the integration value is displayed as a percentage of the predetermined threshold value.

9. The monitoring system of claim 1, wherein the integration value is compared to the predetermined neuropraxia threshold value, the signal comprising an alert or warning indicative of the proximity of the nerve function value to the neuropraxia threshold value and the reversible nature of a nerve injury, and a response comprising the wave form function from a stimulated nerve integrated using a digital algorithm is provided as a display or audible alert regarding a proximity to the neuropraxia threshold value.

10. The monitoring system of claim 1, comprising an EMG device configured to provide a response comprising the wave form function from a stimulated nerve, to integrate said wave form function by a digital algorithm, and to display and/or provide an alert regarding the existence of neuropraxia.

11. The monitoring system of claim 1 having stored therein a patient specific neuropraxia threshold indicator created by digital integration of a voltage response/time waveform, said voltage response/time waveform resulting from an initial stimulation, or series of nerve stimulations, and in which a displayed value of subsequent evoked responses is correlated with a percentage of the predetermined neuropraxia threshold value.

12. The monitoring system of claim 11, wherein the response comprises a free-run electromyography response or a random event waveform nerve response.

13. A monitoring system configured for application to a patient at the time of a potential nerve injuring procedure for detecting, in real time, the existence of fully reversible nerve damage in a targeted nerve, the monitoring system comprising:
   a stimulating component configured for generating an electrical stimulation pulse for stimulating at least the targeted nerve;
   a sensing component configured for detecting a response from one of the stimulated targeted nerve, an evoked nerve and a muscle innervated by the stimulated target nerve;
   a component configured to generate a waveform representative of the detected response;
   a processor programmed to integrate the waveform with respect to time and to provide an integration value;
   a comparator configured for comparing the integration value with a predetermined neuropraxia threshold value and for providing an index value; and
   a display component configured for displaying the index value and signaling a need to discontinue treatment
   wherein the predetermined neuropraxia threshold value represents a nerve response above which nerve damage is fully reversible and below which permanent loss of at least some nerve function occurs.

14. The monitoring system of claim 13, wherein the index value comprises an increasing or decreasing percentage, said percentage representing proximity to the predetermined neuropraxia threshold.

15. The monitoring system of claim 13, further comprising an electromyography device configured for
   a) producing the waveform corresponding to the detected response,
   b) integrating the waveform corresponding to the detected response with respect to time and
   c) providing the integration value using a digital algorithm, for comparing the integration value with the predetermined neuropraxia threshold value and for providing the index value, the system providing an alert indicating the proximity to the neuropraxia threshold.

16. The monitoring system of claim 13, wherein the index value comprises the integration value divided by the predetermined threshold value, said index value indicating the proximity to the neuropraxia threshold.

17. The monitoring system of claim 13 wherein the integration value comprises a real-time integration vale.

* * * * *